United States Patent [19]

Joseph

[11] 4,026,155
[45] May 31, 1977

[54] CONVEYOR SAMPLER

[76] Inventor: John Abraham Joseph, 16 Auckland St., Gladstone, Queensland, Australia

[22] Filed: May 20, 1976

[21] Appl. No.: 688,280

[52] U.S. Cl. ............................................ 73/423 R
[51] Int. Cl.² ........................................ G01N 1/20
[58] Field of Search ................................ 73/423 R

[56] References Cited
UNITED STATES PATENTS

| 2,795,141 | 6/1957 | Pate | 73/423 R |
|---|---|---|---|
| 2,977,800 | 4/1961 | Jordison | 73/423 R |
| 3,110,183 | 11/1963 | Logue | 73/423 R |
| 3,302,769 | 2/1967 | Platzer et al. | 73/423 R X |
| 3,791,218 | 2/1974 | Pennington | 73/423 R |
| 3,875,803 | 4/1975 | Clewlow | 73/423 R |

Primary Examiner—Richard C. Queisser
Assistant Examiner—Joseph W. Roskos
Attorney, Agent, or Firm—Donald D. Jeffery

[57] ABSTRACT

To take cross-section samples of material discharged from a conveyor, a sample chute has its lower end pivoted about an axis parallel to the direction of travel of the material, and at its upper end a cutter head with a mouth leading down to the chute. The sample chute is swung about its axis from one side to the other so the cutter head traverses the discharge end of the conveyor at constant speed, the cutter head mouth being arranged to receive a sample of the discharged material and having sides which are radial to a point on said axis so that, despite the arcuate travel of the cutter head, a true cross-section sample is obtained.

2 Claims, 2 Drawing Figures

CONVEYOR SAMPLER

BACKGROUND OF THE INVENTION

The invention relates to a conveyor sampler, for the purpose of obtaining cross-section samples of material, such as coal, for example, being carried by a conveyor. Samples of such material are often required to be taken at intervals, and rapidly conveyed to a reduction plant where the material taken is divided into the sample required and a balance or residue which may be diverted back to the conveyor. It is desirable that the sample taken should be a true cross-section sample, it should be taken as quickly and cleanly as possible, and that the normal operation of the conveyor should not be interrupted.

SUMMARY OF THE INVENTION

The present invention has been devised with the general object of providing very simple yet efficient apparatus by means of which true cross-section samples may be quickly and easily taken of material carried by a conveyor, such as a conveyor of endless-belt type.

With the foregoing and other objects in view, the invention resides broadly in a conveyor sampler including a main chute, an inlet to the main chute to receive material discharged substantially horizontally thereinto by a conveyor, an outlet from the main chute, a sample chute within the main chute and pivoted, below the inlet to the main chute, about an axis substantially parallel to the direction of flow of the material discharged into the main chute, a cutter head on the upper end of the sample chute, a mouth in the cutter head opening in a direction opposite to that of the flow of material into the main chute, and leading downwardly into the sample chute, and actuating means for oscillating the sample chute to cause the cutter head mouth to be moved across the flow of material into the main chute, the sides of the cutter head mouth being substantially radial to a point on the axis of the sample chute pivot.

BRIEF DESCRIPTION OF THE DRAWINGS

A preferred embodiment of the invention is shown in the accompanying drawings, wherein.

DETAILED DESCRIPTION OF THE PREFERRED EMBODIMENT OF THE INVENTION

Figures 1, 2:
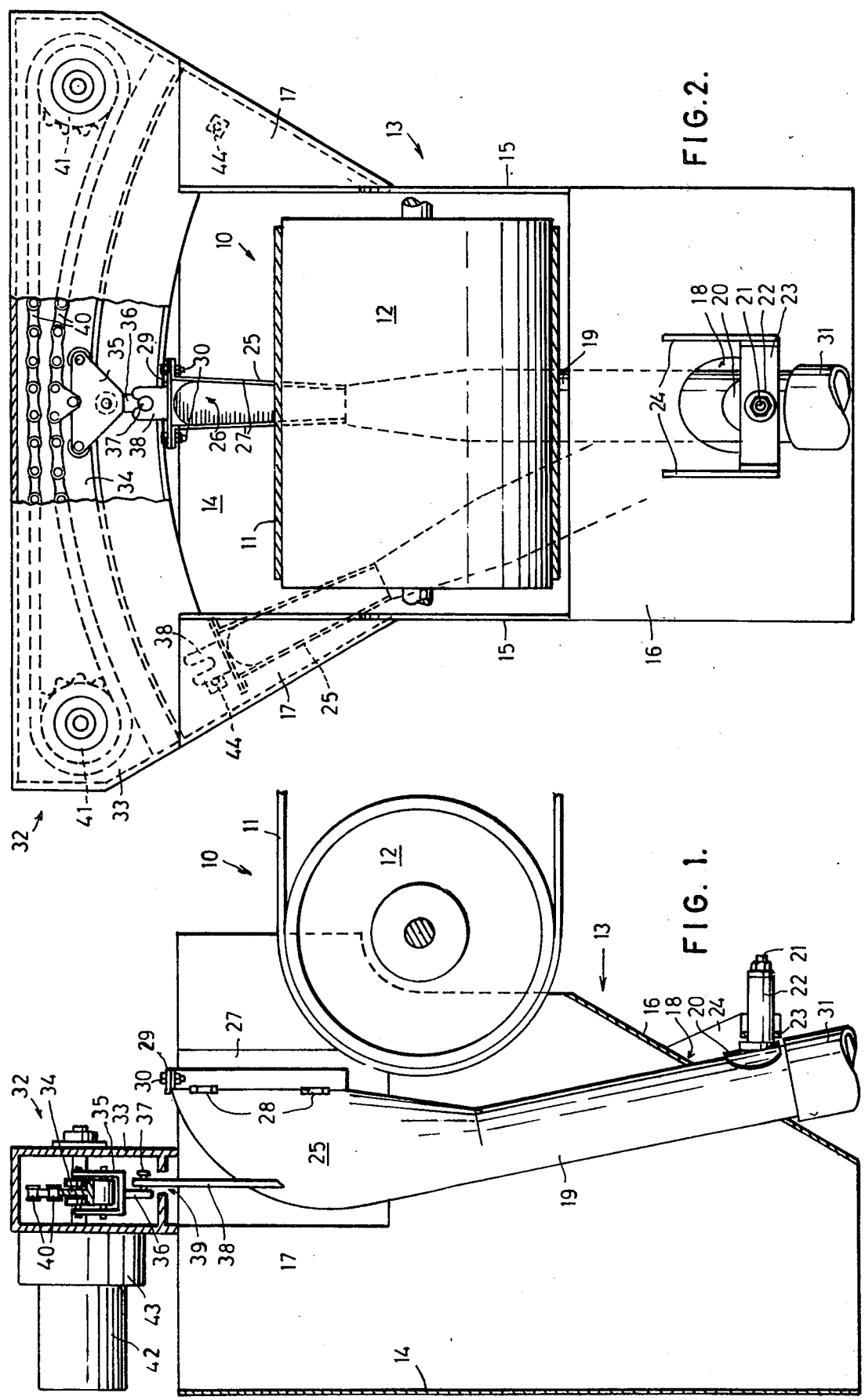
FIG. 1 is a longitudinal sectional view of a conveyor sampler according to the invention.
FIG. 2 is a partly broken away rear view of the sampler shown in FIG. 1.

The apparatus illustrated is associated with a coal conveyor, which includes a primary conveyor, part of which is indicated at 10, this conveyor having an endless belt 11 mounted on rollers, of which one is shown at 12, one of the rollers being driven. The primary conveyor 10 leads at its front or discharge end into the rear of a main chute 13, having a front plate 14, a pair of parallel side plates 15 and a forwardly and downwardly inclining lower rear plate 16, the primary conveyor 10 entering the open upper rear part of the chute. Extensions 17 extend outwardly from the middle upper parts of both sides of the main chute for the purpose hereinafter explained.

An opening 18 is formed through the oblique rear plate 16 and passing fairly closely through this opening is a tubular sample chute 19 of substantially circular cross-section. The sample chute inclines rearwardly and downwardly at a fairly small angle to vertical and, rearwardly of the main chute lower rear plate 16 the sample chute has secured to it a plate 20 to which is rigidly secured a rearwardly extending substantially horizontal pivot 21 which is rotatable in a longitudinal bearing 22 secured through a cross-member 23 fixed between a pair of lugs 24 mounted on the main chute lower rear plate 16. The inclined sample chute 19, then, is oscillatable within the main chute about the horizontal longitudinal axis of the pivot 21.

The sample chute 19 is provided with a cutter head 25 which is more or less in the form of an elbow, with a narrow substantially vertical rearwardly directed inlet or mouth 26 at its upper end, the cutter head developing to a lower end of substantially circular cross-section where it joins the sample chute 19. The cutter head mouth 26 is disposed a short distance forwardly of the upper run of the primary conveyor belt 11. The sides of the cutter head mouth are downwardly convergent, being, in rear view, substantially radial to a point on the axis of the pivot 21. The effective width of the cutter head mouth may be adjustably varied, a pair of rearwardly extending shutters 27 being hinged at 28 to the sides of the mouth and held in adjusted position relative to a top flange 29 on the cutter head 25 by retaining bolts 30.

A flexible conduit 31 is connected to the lower end of the sample chute and leads therefrom to a reduction plant (not shown), the purpose of which is hereinafter explained.

A thruster device 32 is provided for swinging the cutter head 25 to one side or the other as and when required, at a predetermined speed. This device includes a box-like elongated rectangular cover 33 enclosing a transverse rail 34 which is arcuately curved about a centre on the axis of the sample chute pivot 21. A traveller 35 is roller-mounted on the rail 34 and has a downwardly extending lug 36 with a rearwardly extending pin 37 engaged in the bifurcated upper end of an arm 38 rigidly secured to and extending up from the cutter head 25, passing through a transverse slot 39 in the arcuate bottom of the cover 33. A drive mechanism for moving the traveller 35 in one direction or the other along the rail 34 at a constant speed and for automatically bringing it to rest at the end of its travel in either direction includes an endless chain 40 mounted ofn a pair of sprockets 41 within opposite sides of the cover 33, the lower run of the chain being along the arcuate top of the rail 34, and being connected to the traveller 35 at 41. An electric motor 42 drives the shaft of one sprocket 41 through a reduction gearbox 43. When the cutter head 25 is at either end of its travel it is, as shown in broken outline in FIG. 2, clear of the upper run of the primary conveyor belt 11 and largely accommodated within one of the extensions 17 of the main chute 13. At each end of its travel, the arm 38 operates a micro-switch 44 bringing the motor 42 to rest.

The coal carried by the primary conveyor 10 is discharged through the upper rear part of the main chute 13 and descends through the main chute and its open bottom onto a secondary conveyor (not shown) for carrying the coal at a different level and in a different direction from the primary conveyor. The cutter head 25 is normally at rest to one side or the other of the main chute 13 and clear of the path of the coal being discharged from the primary conveyor. Whenever a sample of the coal is to be taken, the motor 42 is operated to drive the thruster traveller 35 to move the cutter head 25 at a constant speed past the flow of coal discharged from the primary conveyor 10. During such movement the cutter head takes through its mouth 26 a cross-section sample of the coal being discharged, this sample being deflected down through the cutter head into the sample chute 19, from which the sample passes gravitationally through the flexible conduit 31 to the reduction plant, (not shown) which is of any suitable known type capable of dividing the material received into a sample, and residue which is diverted to the secondary conveyor. Since the mouth of the cutter head decreases in width from top to bottom, the sample taken with each pass will be a substantially uniform cross-section of the material at the time of taking the sample. The continuous flow of the coal being conveyed is not interrupted, and the kinetic energy of the coal received through the cutter head mouth ensures that this material will, without clogging, pass through the cutter head, sample chute and flexible conduit.

What I claim is:

1. A conveyor sampler including:

a main chute;

an inlet to the main chute adapted to receive materials discharged substantially horizontally thereinto by a conveyor;

an outlet from the main chute;

a sample chute within the main chute pivoted, below the inlet to the main chute, about an axis substantially parallel to the direction of flow of the materials discharged into the main chute;

a cutter head on the upper end of the sample chute;

a mouth in the cutter head directed towards the flow of materials into the main chute, leading downwardly to the sample chute, the sides of the mouth being substantially radial to a point on the axis of the pivot of the sample chute;

means for adjustably varying the effective width of the mouth, and thruster means adapted to oscillate the sample chute to move the cutter head across the flow of materials into the main chute.

2. A conveyor sampler including:

a main chute;

an inlet to the main chute adapted to receive materials discharged substantially horizontally thereinto by a conveyor;

an outlet from the main chute;

a sample chute within the main chute pivoted, below the inlet to the main chute, about an axis substantially parallel to the direction of flow of the materials discharged into the main chute;

a cutter head on the upper end of the sample chute;

a mouth in the cutter head directed towards the flow of the materials into the main chute, and leading downwardly to the sample chute, and thruster means adapted to oscillate the sample chute to move the cutter head across the flow of the materials into the main chute, said thruster means having a rail curved arcuately about a centre on the axis of the pivot of the sample chute, a traveller movable along the rail and operatively connected to the sample chute, and means for driving the traveller along the rail from side to side in either direction.

* * * * *